United States Patent
Reddy et al.

(10) Patent No.: US 7,355,021 B2
(45) Date of Patent: Apr. 8, 2008

(54) SINGLE POT PROCESS FOR THE PREPARATION OF DIAZONAPHTHOQUINONESULFONYL ESTER

(75) Inventors: Vummadi Venkat Reddy, Andhra Pradesh (IN); Boddu Ananda Rao, Andhra Pradesh (IN); Maruthi Janaki Ram Reddy, Andhra Pradesh (IN); Chiguru Srinivas, Andhra Pradesh (IN); Chilukuri Ramesh, Andhra Pradesh (IN); Vaidya Jayathirtha Rao, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 115 days.

(21) Appl. No.: 11/277,006

(22) Filed: Mar. 20, 2006

(65) Prior Publication Data

US 2007/0049742 A1    Mar. 1, 2007

(30) Foreign Application Priority Data

Sep. 1, 2005    (IN)    .................. 2339/DEL/2005

(51) Int. Cl.
C07C 303/26    (2006.01)

(52) U.S. Cl. .................. 534/557; 534/556; 558/44; 558/48

(58) Field of Classification Search ............... 534/556, 534/557; 558/44, 48
See application file for complete search history.

(56) References Cited

U.S. PATENT DOCUMENTS

| 3,149,972 A | 9/1964 | Herrick, Jr. et al. |
| 5,082,932 A | 1/1992 | Siegel et al. |
| 6,559,291 B1 * | 5/2003 | Reddy et al. ............... 534/557 |

FOREIGN PATENT DOCUMENTS

EP    178356    4/1986

* cited by examiner

*Primary Examiner*—Golam M. M. Shameem
(74) *Attorney, Agent, or Firm*—Luedeka, Neely & Graham, PC

(57) ABSTRACT

The present invention provides a single pot process for the preparation of diazonaphthoquinonesulfonyl ester, a useful organic material for micro electronic and dye industry. This study pertains to the one pot preparation of diazonaphthoquinonesulfonyl esters using the corresponding diazonaphthoquinine sulfonic acid or its sodium salt, diphosgene or triphosgene, variety of hydroxy compounds and tertiary organic base in an organic solvent medium.

29 Claims, No Drawings

SINGLE POT PROCESS FOR THE PREPARATION OF DIAZONAPHTHOQUINONESULFONYL ESTER

FIELD OF THE INVENTION

The present invention relates to a single pot process for the preparation of diazonaphthoquinonesulfonyl ester, useful organic materials in micro electronic industry and dye industry. This research pertains to a single-pot process for the preparation of diazonaphthoquinonesulfonyl esters having formula 1 as shown in this drawing below. This is the first report on the single-pot method of preparation of diazonapthoquinonesulfonyl esters. This study pertains to the one pot preparation of diazonaphthoquinonesulfonyl esters (formula 1) using, the corresponding diazonaphthoquinonesulfonic acid or its sodium salt, diphosgene or triphosgene, variety of hydroxy compounds, tertiary organic base and dichloromethane as a solvent medium.

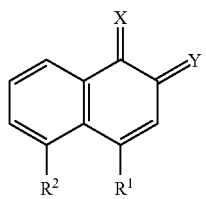

Formula 1 wherein X=O or $N_2$; Y=O or $N_2$; $R^1$=Sulfonyl Ester or H; R2=Sulfonyl ester or H There are a few methods of preparation of these esters available in the literature and some of the reports are discussed below with merits and demerits. All the methods of preparation of these esters reported in the literature involves first preparation of the precursor compound, the corresponding sulfonylchloride and further using the sulfonylchloride to make the sulfonyl ester. Thus, are having two steps in entire preparation of diazonaphthoquinone sulfonyl ester.

One of the methods reported on the preparation of diazonaphthoquinone sulfonyl ester involves first preparation of sulfonylchloride using diazonaphthoquinonesulfonic acid or its sodium salt and chlorosulfonic acid (CA, vol 124, 32490e; PL 161,627, 1993; CA vol. 64, 2033, USSR 173, 756, 1965; J. Park. Chem. 1991, vol. 333, p 467, CA vol. 61, 16218h, year 1964, U.S. Pat. No. 3,149,972). Thus prepared sulfonylchloride was converted in to the corresponding sulfonyl ester using organic base and appropriate R—OH hydroxy compound. This procedure clearly involves two sequential steps; particularly the preparation of sulfonylchloride has disadvantages like, reaction temperature and emission of gases like sulfurdioxide and hydrogen chloride.

Another method involves first preparation of sulfonylchloride using thionylchloride (with DMF as catalyst) and subsequent conversion of sulfonylchloride into the corresponding sulfonyl ester. This method also has two steps in making the sulfonyl ester. The other demerits are like heating the reaction mixture, use of excess thionyl chloride, and evolution of gases like sulfurdioxide and hydrogen chloride (CA vol. 96, 34766b; Khin. Process year 1981, p 505 (Russ)).

Another procedure involves initial preparation of sulfonylchloride using chlorosulfonicacid and thionylchloride and its immediate conversion to the corresponding sulfonyl ester. This procedure is also of two-step process. The disadvantages of this procedure are the same as mentioned in the above discussion (CA, vol. 105, 208620w, Ger (East) 312,180 year 1988; CA vol. 125, 170873d, RO 104,624, year 1994; CA vol. 118, 38553a, year 1993; U.S. Pat. No. 5,082,932, year 1992; CA vol. 106, 105,781x, year 1992; CA vol, 110, 192,455m, year 1989; Pol PL 138,013 year 1987).

Yet another procedure involves is the first preparation of sulfonyl chloride using phosgene (toxic gas) and followed by converting sulfonyl chloride to the corresponding ester. This method has two steps to make sulfonyl ester. The main limitation in this is the use of toxic phosgene gas (CA, vol. 102, 113034d, JP 59,196, 860, year 1984; CA vol. 105, 60439w, EP 178,356, year 1986).

OBJECTIVES OF THE INVENTION

The main objective of the present invention is to provide a single pot process for the preparation of diazonaphthoquinonesulfonyl ester.

Another object of the present invention is to provide is simple and rapid work up process for the isolation of diazonaphthoquinonesulfonyl ester.

Yet another object of the present invention is to provide diazonaphthoquinonesulfonyl ester having purity >96%.

SUMMARY OF THE INVENTION

The present invention illustrates an altogether single-pot process for the preparation of diazonaphthoquinonesulfonyl esters by reacting the corresponding diazonaphthoquinonesulfonic acid or its sodium salt either with diphosgene or with triphosgene in the presence of triethylamine (organic base) and dichloromethane as a solvent or medium. This reaction is followed by the addition of hydroxy compound (R—OH) and triethylamine, in the same pot leading to the diazonaphthaquinonesulfonyl ester formation. Various solvents like, chloroform, 1,2-dichloroethane, benzene, toluene, acetonitrile, benzonitrile, nitrobenzene etc., and others are also used. Organic bases like tributylamine pyridine, tripropylamine, N,N-dimethylaniline, N,N-diethylaniline etc., and other organic bases are also employed. Dichloromethane as solvent and triethylamine as base were preferred. The temperature of the reaction was varied over a range of −50° C. to +10° C. and ~0° C. is the preferred temperature condition. The organic base is found to be essential for conducting the reaction and the base has to be of tertiary base in nature. The mole ratio, maintained in the reaction is found to be a right combination. The reaction is conveniently monitored by UV-Visible absorption spectrometry. The work up procedure and isolation of product "diazonaphthoquinonesulfonyl ester" is simple and rapid. The purity of the product is >96% as judged by HPLC and UV-Visible absorption measurements. The diazonaphthoquinonesulfonyl ester prepared was photolyzed (Q 366 nm) in methanol solvent to confirm its photoactivating property. Products were characterized by the spectral data.

DETAIL DESCRIPTION OF THE INVENTION

Accordingly the present invention provides a single pot process for the preparation of diazonaphtoquinonesulfonyl ester having the general formula 1, which comprises

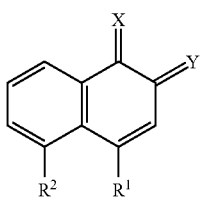

Formula 1

Wherein X=O or N₂; Y=O or N₂; R¹=Sulfonyl ester or H; R²=Sulfonyl ester or H reacting diazonaphthoquinonesulfonic acid or its sodium salt with triphosgene or diphosgene in an organic solvent, in the presence of tertiary organic base, at a temperature in the range of −50 to −30° C., for a period of about 1 hr, bringing the temperature of the above said reaction mixture to about 0° C., adding subsequently a hydroxyl compound and a tertiary organic base taken in an organic solvent to the above said reaction mixture, followed by stirring for another about 1 hr, distilling off the organic solvent and tertiary organic base under vacuum, at a temperature in the range of 25-30° C. to obtain the desired product.

In an embodiment of the present invention the diazonaphthoquinonesulfonic acid used is selected from the group consisting of 2-diazo-1-naphthoquinone-4-sulfonic acid, 2-diazo-1-naphthoquinone-5-sulfonic acid and 1-diazo-2-naphthoquinone-4-sulfonic acid.

In another embodiment of the present invention the tertiary organic base used is selected from the group consisting of triethylamine, tributylamine, tripropylamine, pyridine, alkyl-pyridines, piperidine, N-methyl piperidine, N-ethyl piperidine, N-butyl piperidine, substituted piperidines, diazabicyclooctane, diazabicycloundacene, dimethylaminopyridines, triazoles, imidazoles, triphenylphosphine, 4-N,N-dimethylaminopyridine, 4-N,N-diethylamino pyridine, N,N-dimethylaniline, N,N-diethylaniline, substituted anilines, N-methylpyrrolidine, pyrrolidines, N-methylmorpholine, and N-methylindole.

In yet another embodiment the organic solvent used is selected from the group consisting of dichloromethane, chloroform, 1,2-dichloroethane, organochlorine solvents, benzene, toluene, xylenes, aromatic hydrocarbon, acetonitrile, benzonitrile, nitrobenzene, 1,4-dioxane, carbon tetrachloride, dimethyl formamide, chlorobenzene, tetrahydrofuran, dialkylethers, alkyl-aryl ether, diarylethers, dimethylsulphoxide and o-dichlorobenzene.

In yet another embodiment the hydroxyl compound used is selected from the group consisting of phenol, o-cresol, m-cresol, p-cresol, resorcinol, phloroglucinol, 2,3-xylenol, 2,5-xylenol, 3,5-xylenol, 3,4-xylenol, o-ethyl phenol, m-ethyl phenol, p-ethyl phenol, 2,3,4-trimethyl phenol, 2,3,5-trimethyl phenol, 2-ter. butyl phenol, 2-ter. butyl-4-methyl phenol, 2-ter butyl-5-methyl phenol, p-ethoxy phenol, m-ethoxy phenol, p-propoxy phenol, m-propoxy phenol, o-isopropyl phenol, p-isopropyl phenol, 2-methyl-4-isopropenyl phonone, 3,5-dimethoxy phenol, 2-methoxy-4-methyl phenol, p-butoxy phenol, m-butoxy phenol, 2-ethyl 4-isopropenyl phenol, 4-phenyl phenol, 4,4¹-dihydroxy biphenyl, Hydroquinone, Pyrogallol, 2,4-dihydroxy benzophenone, 2,4,2¹,4¹-tetrahydroxy biphenylsulphide, 2,2¹-dihydroxy di naphthyl methane, 4,6-bis[2,4-dihydroxy phenyl thio]resorcinol, 2,4-dihydroxy-3,5-dibromo benzophenone, o-xylenol, m-xylenol, p-xylenol, 1,2,3 trihydroxybenzene, 1,3,5 trihydroxybenzene, 1,2,4, trihydroxybenzene, trihydroxybenzophenone, salicylaldehyde, p-hydroxy benzaldehyde, 4,4' dihydroxybenzophenone, o-chlorophenol, m-chlorophenol, p-chlorophenol, dichlorophenols, α-naphthol, β-naphthol, methanol, ethanol, isopropanol, butanol, propanol, isobutanol and t-butanol.

In yet another embodiment the molar ratio of diazonaphthoquinonesulfonic acid or its sodium salt to triphosgene or diphosgene used is in the range of 1:1 to 1:1.5.

In yet another embodiment the molar ratio of diazonaphthoquinone sulfonic acid or its sodium salt to organic base used is in the rang of 1:3 to 1:5.

In yet another embodiment the molar ratio of diazonaphthoquinone sulfonic acid or its sodium salt to hydroxyl compound used is in the range of 1:0.8 to 1:2.

In yet another embodiment the reaction temperature used is preferably −40° C.

The following examples are given by way of illustration of the present invention and therefore should not be construed to limit the scope of the present invention

EXAMPLE 1

2-Diazo-1-naphthoquinone-4-sulfonic acid sodium salt (2.72 g: 0.01 mol) was taken in to 25 ml of dichloromethane and cooled to 50° C. Added triethylamine (2.02 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml dichloromethane and followed by triethylamine (2.02 g, 0.02 mol) in 3 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, Na₂CO₃ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 2

2-Diazo-1-naphthoquinone-5-sulfonic acid sodium salt (2.72 g: 0.01 mol) was taken in to 25 ml of dichloromethane and cooled to −50° C. Added triethylamine (2.02 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (0.85 g; 0.009 mol) in 3 ml dichloromethane and followed by triethylamine (2.02 g, 0.02 mol) in 3 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 3

1-Diazo-2-naphthoquinone-4-sulfonic acid sodium salt (2.72 g: 0.01 mol) was taken in to 25 ml of dichloromethane and cooled to −50° C. Added triethylamine (2.02 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 1-diazo-2-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml dichloromethane and followed by triethylamine (2.02 g, 0.02 mol) in 3 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 4

2-Diazo-1-naphthoquinone-4-sulfonic acid sodium salt (2.72 g: 0.01 mol) was taken in to 25 ml of dichloromethane and cooled to −50° C. Added pyridine (1.58 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml dichloromethane and followed by pyridine (1.58 g, 0.02 mol) in 3 ml dichloromethane. Stirring was continued for the 60 min at 0° C. Reaction mixture was brought to room temperature, dichloromethane and pyridine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 5

2-Diazo-1-naphthoquinone-5-sulfonic acid sodium salt (2.72 g: 0.01 mol) was taken in to 25 ml of dichloromethane and cooled to −50° C. Added pyridine (1.58 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at 50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (0.85 g; 0.009 mol) in 3 ml dichloromethane and followed by pyridine (1.58 g, 0.02 mol) in 3 ml dichloromethane. Stirring was continued for the 60 min at 0° C. Reaction mixture was brought to room temperature, dichloromethane and pyridine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 6

1-Diazo-2-naphthoquinone-4-sulfonic acid sodium salt (2.72 g: 0.01 mol) was taken in to 25 ml of dichloromethane and cooled to −50° C. Added pyridine (1.58 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (0.85 g;

0.009 mol) in 3 ml dichloromethane and followed by pyridine (1.58 g, 0.02 mol) in 3 ml dichloromethane. Stirring was continued for the 60 min at 0° C. Reaction mixture was brought to room temperature, dichloromethane and pyridine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 7

2-Diazo-1-naphthoquinone-4-sulfonic acid sodium salt (27.2 g: 0.1 mol) was taken in to 250 ml of dichloromethane and cooled to −50° C. Added triethylamine (20.2 g, 0.2 mol) to the above solution and maintained the temperature at −50° C. Then added triphosgene (32 g, 0.1 µmol) in 100 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (8.5 g; 0.09 mol) in 30 ml dichloromethane and followed by triethylamine (20.2 g, 0.2 mol) in 30 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (9.0 g, $Na_2CO_3$ in 250 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 8

2-Diazo-1-naphthoquinone-5-sulfonic acid sodium salt (27.2 g: 0.1 mol) was taken in to 250 ml of dichloromethane and cooled to −50° C. Added triethylamine (20.2 g, 0.2 mol) to the above solution and maintained the temperature at −50° C. Then added triphosgene (32 g, 0.011 mol) in 100 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (8.5 g; 0.09 mol) in 30 ml dichloromethane and followed by triethylamine (20.2 g, 0.2 mol) in 30 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (9.0 g, $Na_2CO_3$ in 250 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 9

2-Diazo-1-naphthoquinone-4-sulfonic acid sodium salt (54.4 g: 0.2 mol) was taken in to 350 ml of dichloromethane and cooled to −50° C. Added triethylamine (40.4 g, 0.4 mol) to the above solution and maintained the temperature at −50° C. Then added triphosgene (64 g, 0.22 mol) in 100 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (17 g; 0.18 mol) in 60 ml dichloromethane and followed by triethylamine (40.4 g, 0.4 mol) in 60 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (18.0 g, $Na_2CO_3$ in 500 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 10

2-Diazo-1-naphthoquinone-5-sulfonic acid sodium salt (54.4 g: 0.2 mol) was taken in to 350 ml of dichloromethane and cooled to −50° C. Added triethylamine (40.4 g, 0.4 mol) to the above solution and maintained the temperature at −50° C. Then added triphosgene (64 g, 0.22 mol) in 100 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (17 g; 0.18 mol) in 60 ml dichloromethane and followed by triethylamine (40.4 g, 0.4 mol) in 60 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (18.0 g, $Na_2CO_3$ in 500 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 11

2-Diazo-1-naphthoquinone-5-sulfonic acid sodium salt (27.2 g: 0.1 mol) was taken in to 250 ml of dichloromethane and cooled to −50° C. Added triethylamine (20.2 g, 0.2 mol) to the above solution and maintained the temperature at −50° C. Then added diphosgene (21.78 g, 0.011 mol) in 100 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (8.5 g; 0.09 mol) in 30 ml dichloromethane and followed by triethylamine (20.2 g, 0.2 mol) in 30 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (9.0 g, $Na_2CO_3$ in 250 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 12

2-Diazo-1-naphthoquinone-4-sulfonic acid sodium salt (2.72 g: 0.01 mol) was taken in to 25 ml of chloroform and cooled to −50° C. Added triethylamine (2.02 g, 0.02 mol) to the above solution and maintained the temperature at −50° C. Then added triphosgene (3.2 g, 0.011 mol) in 15 ml chloroform very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml chloroform and followed by triethylamine (2.02 g, 0.02 mol) in 3 ml chloroform. Stirring was continued for the 60 min at 0° C. Reaction mixture was brought to room temperature, chloroform and triethylamine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 13

2-Diazo-1-naphthoquinone-5-sulfonic acid sodium salt (2.72 g: 0.01 mol) was taken in to 25 ml of chloroform and cooled to −50° C. Added triethylamine (2.02 g, 0.02 mol) to the above solution and maintained the temperature at −50° C. Then added triphosgene (3.2 g, 0.011 mol) in 15 ml chloroform very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (0.85 g; 0.009 mol) in 3 ml chloroform and followed by triethylamine (2.02 g, 0.02 mol) in 3 ml chloroform. Stirring was continued for the 60 min at 0° C. Reaction mixture was brought to room temperature, chloroform and triethylamine was distilled off at room temperature under vacuum. The remaining solid residue was mixed with cold soda water (0.9 g, $Na_2CO_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 14

1-Diazo-2-naphthoquinone-4-sulfonic acid sodium salt (2.72 g: 0.01 mol) was taken in to 25 ml of chloroform and cooled to 50° C. Added triethylamine (2.02 g, 0.02 mol) to the above solution and maintained the temperature at −50° C. Then added triphosgene (3.2 g, 0.011 mol) in 15 ml chloroform very slowly and maintaining the temperature at −50° C. with stirring over a period of 20 min. The reaction mixture was stirred magnetically for 60 min at −50° C. and then the reaction mixture was brought to 0° C. The conversion of 1-diazo-2-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml chloroform and followed by triethylamine (2.02 g, 0.02 mol) in 3 ml chloroform. Stirring was continued for the 60 min at 0° C. Reaction mixture was brought to room temperature, chloroform and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 15

2-Diazo-1-naphthoquinone-4-sulfonic acid sodium salt (2.72 g: 0.01 mol) was taken in to 25 ml of 1,2-dichloroethane and cooled to −50° C. Added triethylamine (2.02 g, 0.02 mol) to the above solution and maintained the temperature at −50° C. Then added triphosgene (3.2 g, 0.011 mol) in 15 ml 1,2-dichloroethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml 1,2-dichloroethane and followed by triethylamine (2.02 g, 0.02 mol) in 3 ml 1,2-dichloroethane. Stirring was continued for the 60 min at 0° C. Reaction mixture was brought to room temperature, 1,2-dichloroethane and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 16

2-Diazo-1-naphthoquinone-5-sulfonic acid sodium salt (2.72 g: 0.01 mol) was taken in to 25 ml of 1,2-dichloroethane and cooled to −50° C. Added triethylamine (2.02 g, 0.02 mol) to the above solution and maintained the temperature at −50° C. Then added triphosgene (3.2 g, 0.011 mol) in 15 ml 1,2-dichloroethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (0.85 g; 0.009 mol) in 3 ml 1,2-dichloroethane and followed by triethylamine (2.02 g, 0.02 mol) in 3 ml 1,2-dichloroethane. Stirring was continued for the 60 min at 0° C. Reaction mixture was brought to room temperature, 1,2-dichloroethane and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 17

1-Diazo-2-naphthoquinone-4-sulfonic acid sodium salt (2.72 g: 0.01 mol) was taken in to 25 ml of 1,2-dichloroethane and cooled to −50° C. Added triethylamine (2.02 g, 0.02 mol) to the above solution and maintained the temperature at −50° C. Then added triphosgene (3.2 g, 0.011 mol) in 15 ml 1,2-dichloroethane very slowly and maintaining the temperature at −50° C. with stirring over a period of 20 min. The reaction mixture was stirred magnetically for 60 min at −50° C. and then the reaction mixture was brought to 0° C. The conversion of 1-diazo-2-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml 1,2-dichloroethane and followed by triethylamine (2.02 g, 0.02 mol) in 3 ml 1,2-dichloroethane. Stirring was continued for the 60 min at 0° C. Reaction mixture was brought to room temperature, 1,2-dichloroethane and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 18

2-Diazo-1-naphthoquinone-4-sulfonic acid sodium salt (2.72 g: 0.01 mol) was taken in to 25 ml of acetonitrile and cooled to −50° C. Added triethylamine (2.02 g, 0.02 mol) to the above solution and maintained the temperature at −50° C. Then added triphosgene (3.2 g, 0.011 mol) in 15 ml acetonitrile very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml acetonitrile and followed by triethylamine (2.02 g, 0.02 mol) in 3 ml acetonitrile. Stirring was continued for the 60 min at 0° C. Reaction mixture was brought to room temperature, acetonitrile and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 19

2-Diazo-1-naphthoquinone-5-sulfonic acid sodium salt (2.72 g: 0.01 mol) was taken in to 25 ml of acetonitrile and cooled to −50° C. Added triethylamine (2.02 g, 0.02 mol) to the above solution and maintained the temperature at −50° C. Then added triphosgene (3.2 g, 0.011 mol) in 15 ml acetonitrile very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added phenol (0.85 g; 0.009 mol) in 3 ml acetonitrile and followed by triethylamine (2.02 g, 0.02 mol) in 3 ml acetonitrile. Stirring was continued for the 60 min at 0° C. Reaction mixture was brought to room temperature, acetonitrile and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 20

1-Diazo-2-naphthoquinone-4-sulfonic acid sodium salt (2.72 g: 0.01 mol) was taken in to 25 ml of acetonitrile and cooled to −50° C. Added triethylamine (2.02 g, 0.02 mol) to the above solution and maintained the temperature at −50° C. Then added triphosgene (3.2 g, 0.011 mol) in 15 ml acetonitrile very slowly and maintaining the temperature at −50° C. with stirring over a period of 20 min. The reaction mixture was stirred magnetically for 60 min at −50° C. and then the reaction mixture was brought to 0° C. The conversion of 1-diazo-2-naphthoquinone-4-sulfonic acid or its sodium salt to the corresponding sulfonylchloride can be conveniently monitored by UV-Visible absorption spectrometry. To the same reaction pot added phenol (0.85 g; 0.009 mol) in 3 ml acetonitrile and followed by triethylamine (2.02 g, 0.02 mol) in 3 ml acetonitrile. Stirring was continued for the 60 min at 0° C. Reaction mixture was brought to room temperature, acetonitrile and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 21

2-Diazo-1-naphthoquinone-5-sulfonic acid sodium salt (2.72 g: 0.01 mol) was taken in to 25 ml of dichloromethane and cooled to −50° C. Added triethylamine (2.02 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added methanol (0.30 g; 0.009 mol) in 3 ml dichloromethane and followed by triethylamine (2.02 g, 0.02 mol) in 3 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 22

2-Diazo-1-naphthoquinone-5-sulfonic acid sodium salt (2.72 g: 0.01 mol) was taken in to 25 ml of dichloromethane and cooled to −50° C. Added triethylamine (2.02 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added ethanol (0.42 g; 0.009 mol) in 3 ml dichloromethane and followed by triethylamine (2.02 g, 0.02 mol) in 3 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

EXAMPLE 23

2-Diazo-1-naphthoquinone-5-sulfonic acid sodium salt (2.72 g: 0.01 mol) was taken in to 25 ml of dichloromethane and cooled to −50° C. Added triethylamine (2.02 g, 0.02 mol) to the above solution and maintained the temperature at −50° C. Then added triphosgene (3.2 g, 0.011 mol) in 15 ml dichloromethane very slowly and maintaining the temperature at −50° C. with stirring over a period of 20 min. The reaction mixture was stirred magnetically for 60 min at −50° C. and then the reaction mixture was brought to 0° C. The conversion of 2-diazo-1-naphthoquinone-5-sulfonic acid or its sodium salt to the corresponding sulfonylchloride can be conveniently monitored by UV-Visible absorption spectrometry. To the same reaction pot added propanol (0.55 g; 0.009 mol) in 3 ml dichloromethane and followed by triethylamine (2.02 g, 0.02 mol) in 3 ml dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, Na$_2$CO$_3$ in 25 ml water) and stirred for 10 min. The solid was filtered, washed with copious amounts of water and dried in a vacuum desiccator containing phosphorus pentoxide. All these operations were conducted in a yellow room/dark room. After the isolation of the ester product, it was photolysed (366 nm) to ascertain photoactivating property. The ester formation can be conveniently monitored by UV-Visible absorption spectrometry. The product was characterized by spectral data. The yield is >92%, purity >96%. The purity of the ester can be determined using reverse phase HPLC.

ADVANTAGES

The various advantages of this process are given below:

1. This is a single-pot process for the synthesis of diazonaphthoquinonesulfonyl ester, thus avoiding the two step process.

2. It is superior to the existing two step process in reducing the time of preparation.

3. The reaction conditions are very mild like temperature of reaction is ~50° C. to 0° C.

4. This is a simple work up procedure leading to high purity product.

5. Variety of hydroxy compounds can be used in this single-pot preparation of sulfonyl ester.

We claim:

1. A single pot process for the preparation of diazonaphthoquinonesulfonyl ester having the general formula 1, which comprises

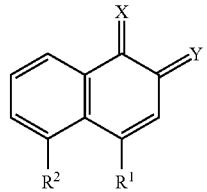

Formula 1 wherein X=O or N$_2$: R$^1$=Sulfonyl ester or H; R$^2$=Sulfonyl ester or H reacting diazonaphthoquinonesulfonic acid or its sodium salt with triphosgene or diphosgene in an organic solvent, in the presence of tertiary organic base, at a temperature in the range of −50 to −30° C., for a period of about 1 hr, bringing the temperature of the above said reaction mixture to about 0° C., adding subsequently a hydroxyl compound and a tertiary organic base taken in an organic solvent to the above said reaction mixture, followed by stirring for another about 1 hr, distilling off the organic solvent and tertiary organic base under vacuum, at a temperature in the range of 25-30° C. to obtain the desired product.

2. A process according to claim 1, wherein the diazonaphthoquinonesulfonic acid used is selected from the group consisting of 2-diazo-1-naphthoquinone-4-sulfonic acid, 2-diazo-1-naphthoquinone-5-sulfonic acid and 1-diazo-2-naphthoquinone-4-sulfonic acid.

3. A process according to claim 2, wherein the tertiary organic base used is selected from the group consisting of triethylamine, tributylamine, tripropylamine, pyridine, alkyl pyridines, piperidine, N-methyl piperidine, N-ethyl piperidine, N-butyl piperidine, substituted piperidines, diazabicyclooctane, diazabicycloundacene, dimethylaminopyridines, triazoles, imidazoles, triphenylphosphine, 4-N, N-dimethylaminopyridine, 4-N,N-diethylamino pyridine, N,N-dimethylaniline, N,N-diethylaniline, substituted anilines, N-methylpyrrolidine, pyrrolidines, N-methylmorpholine, and N-methylindole.

4. A process according to claim 3, wherein the organic solvent used is selected from the group consisting of dichloromethane, chloroform, 1,2-dichloroethane, organochlorine solvents, benzene, toluene, xylenes, aromatic hydrocarbon, acetonitrile, benzonitrile, nitrobenzene, 1,4-dioxane, carbon tetrachloride, dimethyl formamide, chlorobenzene, tetrahydrofuran, dialkylethers, alkyl-aryl ether, diarylethers, dimethylsulphoxide and o-dichlorobenzene.

5. A process according to claim 4, wherein the hydroxyl compound used is selected from the group consisting of phenol, o-cresol, m-cresol, p-cresol, resorcinol, phloroglucinol, 2,3-xylenol, 2,5-xylenol, 3,5-xylenol, 3,4-xylenol, o-ethyl phenol, m-ethyl phenol, p-ethyl phenol, 2,3,4-trimethyl phenol, 2,3,5-trimethyl phenol, 2-ter. butyl phenol, 2-ter. butyl-4-methyl phenol, 2-ter butyl-5-methyl phenol, p-ethoxy phenol, methoxy phenol, p-propoxy phenol, m-propoxy phenol, o-isopropyl phenol, p-isopropyl phenol, 2-methyl-4-isopropenyl phonone, 3,5-dimethoxy phenol, 2-methoxy-4-methyl phenol, p-butoxy phenol, m-butoxy phenol, 2-ethyl 4-isopropenyl phenol, 4-phenyl phenol, 4,4'-dihydroxy biphenyl, Hydroquinone, Pyrogallol, 2,4-dihydroxy benzophenone, 2,4,2',4'-tetrahydroxy biphenylsulphide, 2,2'-dihydroxy di naphthyl methane, 4,6-bis[2,4-dihydroxy phenyl thio]resorcinol, 2,4-dihydroxy-3,5-dibromo benzophenone, o-xylenol, m-xylenol, p-xylenol, 1,2,3 trihydroxybenzene, 1,3,5 trihydroxybenzene, 1,2,4, trihydroxybenzene, trihydroxybenzophenone, salicylaldehyde, p-hydroxy benzaldehyde, 4,4' dihydroxybenzophenone, o-chlorophenol, m-chlorophenol, p-chlorophenol, dichlorophenols, α-naphthol, β-naphthol, methanol, ethanol, isopropanol, butanol, propanol, isobutanol and 1-butanol.

6. A process according to claim 5, wherein the molar ratio of diazonaphthoquinonesulfonic acid or its sodium salt to triphosgene or diphosgene used is in the range of 1:1 to 1:1.5.

7. A process according to claim 6, wherein the molar ratio of diazonaphthoquinone sulfonic acid or its sodium salt to organic base used is in the range of 1:3 to 1:5.

8. A process according to claim 7, wherein the molar ratio of diazonaphthoquinone sulfonic acid or its sodium salt to hydroxyl compound used is in the range of 1:0.8 to 1:2.

9. A process according to claim 1, wherein the tertiary organic base used is selected from the group consisting of triethylamine, tributylamine, tripropylamine, pyridine, alkyl pyridines, piperidine, N-methyl piperidine, N-ethyl piperidine, N-butyl piperidine, substituted piperidines, diazabicyclooctane, diazabicycloundacene, dimethylaminopyridines, triazoles, imidazoles, triphenylphosphine, 4-N,N-dimethylaminopyridine, 4-N,N-diethylamino pyridine, N,N-dimethylaniline, N,N-diethylaniline, substituted anilines, N-methylpyrrolidine, pyrrolidines, N-methylmorpholine, and N-methylindole.

10. A process according to claim 1, wherein the organic solvent used is selected from the group consisting of dichloromethane, chloroform, 1,2-dichloroethane, organochlorine solvents, benzene, toluene, xylenes, aromatic hydrocarbon, acetonitrile, benzonitrile, nitrobenzene, 1,4-dioxane, carbon tetrachloride, dimethyl formamide, chlorobenzene, tetrahydrofuran, dialkylethers, alkyl-aryl ether, diarylethers, dimethylsulphoxide and o-dichlorobenzene.

11. A process according to claim 2, wherein the organic solvent used is selected from the group consisting of dichloromethane, chloroform, 1,2-dichloroethane, organochlorine solvents, benzene, toluene, xylenes, aromatic hydrocarbon, acetonitrile, benzonitrile, nitrobenzene, 1,4-dioxane, carbon tetrachloride, dimethyl formamide, chlorobenzene, tetrahydrofuran, dialkylethers, alkyl-aryl ether, diarylethers, dimethylsulphoxide and o-dichlorobenzene.

12. A process according to claim 1, wherein the hydroxyl compound used is selected from the group consisting of phenol, o-cresol, m-cresol, p-cresol, resorcinol, phloroglucinol, 2,3-xylenol, 2,5-xylenol, 3,5-xylenol, 3,4-xylenol, o-ethyl phenol, m-ethyl phenol, p-ethyl phenol, 2,3,4-trimethyl phenol, 2,3,5-trimethyl phenol, 2-ter. butyl phenol, 2-ter. butyl-4-methyl phenol, 2-ter butyl-5-methyl phenol, p-ethoxy phenol, methoxy phenol, p-propoxy phenol, m-propoxy phenol, o-isopropyl phenol, p-isopropy phenol, 2-methyl-4-isopropenyl phonone. 3,5-dimethoxy phenol, 2-methoxy-4-methyl phenol, p-butoxy phenol, m-butoxy phenol, 2-ethyl 4-isopropenyl phenol, 4-phenyl phenol, 4,4'-dihydroxy biphenyl, Hydroquinone, Pyrogallol, 2,4-dihydroxy benzophenone, 2,4,2',4'-tetrahydroxy biphenylsulphide, 2,2'-dihydroxy di naphthyl methane, 4,6-bis[2,4-dihydroxy phenyl thio]resorcinol, 2,4-dihydroxy-3,5-dibromo benzophenone, o-xylenol, m-xylenol, p-xylenol, 1,2,3 trihydroxybenzene, 1,3,5 trihydroxybenzene, 1,2,4, trihydroxybenzene, trihydroxybenzophenone, salicylaldehyde, p-hydroxy benzaldehyde, 4,4' dihydroxybenzophenone, o-chlorophenol, m-chlorophenol, p-chlorophenol, dichlorophenols, α-naphthol, β-naphthol, methanol, ethanol, isopropanol, butanol, propanol, isobutanol and 1-butanol.

13. A process according to claim 2, wherein the hydroxyl compound used is selected from the group consisting of phenol, o-cresol, m-cresol, p-cresol, resorcinol, phloroglucinol, 2,3-xylenol, 2,5-xylenol, 3,5-xylenol, 3,4-xylenol, o-ethyl phenol, m-ethyl phenol, p-ethyl phenol, 2,3,4-trimethyl phenol, 2,3,5-trimethyl phenol, 2-ter. butyl phenol, 2-ter. butyl-4-methyl phenol, 2-ter butyl-5-methyl phenol, p-ethoxy phenol, methoxy phenol, p-propoxy phenol, m-propoxy phenol, o-isopropyl phenol, p-isopropy phenol, 2-methyl-4-isopropenyl phonone, 3,5-dimethoxy phenol, 2-methoxy-4-methyl phenol, p-butoxy phenol, m-butoxy phenol, 2-ethyl 4-isopropenyl phenol, 4-phenyl phenol, 4,4'-dihydroxy biphenyl, Hydroquinone, Pyrogallol, 2,4-dihydroxy benzophenone, 2,4,2',4'-tetrahydroxy biphenylsulphide, 2,2'-dihydroxy di naphthyl methane, 4,6-bis[2,4-dihydroxy phenyl thio]resorcinol, 2,4-dihydroxy-3,5-dibromo benzophenone, o-xylenol, m-xylenol, p-xylenol, 1,2,3 trihydroxybenzene, 1,3,5 trihydroxybenzene, 1,2,4, trihydroxybenzene, trihydroxybenzophenone, salicylaldehyde, p-hydroxy benzaldehyde, 4,4' dihydroxybenzophenone, o-chlorophenol, m-chlorophenol, p-chlorophenol, dichlorophenols, α-naphthol, β-naphthol, methanol, ethanol, isopropanol, butanol, propanol, isobutanol and 1-butanol.

14. A process according to claim 3, wherein the hydroxyl compound used is selected from the group consisting of phenol, o-cresol, m-cresol, p-cresol, resorcinol, phloroglucinol, 2,3-xylenol, 2,5-xylenol, 3,5-xylenol, 3,4-xylenol, o-ethyl phenol, m-ethyl phenol, p-ethyl phenol, 2,3,4-trimethyl phenol, 2,3,5-trimethyl phenol, 2-ter. butyl phenol, 2-ter. butyl-4-methyl phenol, 2-ter butyl-5-methyl phenol, p-ethoxy phenol, methoxy phenol, p-propoxy phenol, m-propoxy phenol, o-isopropyl phenol, p-isopropy phenol, 2-methyl-4-isopropenyl phonone, 3,5-dimethoxy phenol, 2-methoxy-4-methyl phenol, p-butoxy phenol, m-butoxy phenol, 2-ethyl 4-isopropenyl phenol, 4-phenyl phenol, 4,4'-dihydroxy biphenyl, Hydroquinone, Pyrogallol, 2,4-dihydroxy benzophenone, 2,4,2',4'-tetrahydroxy biphenylsulphide, 2,2'-dihydroxy di naphthyl methane, 4,6-bis[2,4-dihydroxy phenyl thio]resorcinol, 2,4-dihydroxy-3,5-dibromo benzophenone, o-xylenol, m-xylenol, p-xylenol, 1,2,3 trihydroxybenzene, 1,3,5 trihydroxybenzene, 1,2,4, trihydroxybenzene, trihydroxybenzophenone, salicylaldehyde, p-hydroxy benzaldehyde, 4,4' dihydroxybenzophenone, o-chlorophenol, m-chlorophenol, p-chlorophenol, dichlorophenols, α-naphthol, β-naphthol, methanol, ethanol, isopropanol, butanol, propanol, isobutanol and 1-butanol.

15. A process according to claim 1, wherein the molar ratio of diazonaphthoquinonesulfonic acid or its sodium salt to triphosgene or diphosgene used is in the range of 1:1 to 1:1.5.

16. A process according to claim 2, wherein the molar ratio of diazonaphthoquinonesulfonic acid or its sodium salt to triphosgene or diphosgene used is in the range of 1:1 to 1:1.5.

17. A process according to claim 3, wherein the molar ratio of diazonaphthoquinonesulfonic acid or its sodium salt to triphosgene or diphosgene used is in the range of 1:1 to 1:1.5.

18. A process according to claim 4, wherein the molar ratio of diazonaphthoquinonesulfonic acid or its sodium salt to triphosgene or diphosgene used is in the range of 1:1 to 1:1.5.

19. A process according to claim 1, wherein the molar ratio of diazonaphthoquinone sulfonic acid or its sodium salt to organic base used is in the range of 1:3 to 1:5.

20. A process according to claim 2, wherein the molar ratio of diazonaphthoquinone sulfonic acid or its sodium salt to organic base used is in the range of 1:3 to 1:5.

21. A process according to claim 3, wherein the molar ratio of diazonaphthoquinone sulfonic acid or its sodium salt to organic base used is in the range of 1:3 to 1:5.

22. A process according to claim 4, wherein the molar ratio of diazonaphthoquinone sulfonic acid or its sodium salt to organic base used is in the range of 1:3 to 1:5.

23. A process according to claim 5, wherein the molar ratio of diazonaphthoquinone sulfonic acid or its sodium salt to organic base used is in the range of 1:3 to 1:5.

24. A process according to claim 1, wherein the molar ratio of diazonaphthoquinone sulfonic acid or its sodium salt to hydroxyl compound used is in the range of 1:0.8 to 1:2.

25. A process according to claim 2, wherein the molar ratio of diazonaphthoquinone sulfonic acid or its sodium salt to hydroxyl compound used is in the range of 1:0.8 to 1:2.

26. A process according to claim 3, wherein the molar ratio of diazonaphthoquinone sulfonic acid or its sodium salt to hydroxyl compound used is in the range of 1:0.8 to 1:2.

27. A process according to claim 4, wherein the molar ratio of diazonaphthoquinone sulfonic acid or its sodium salt to hydroxyl compound used is in the range of 1:0.8 to 1:2.

28. A process according to claim 5, wherein the molar ratio of diazonaphthoquinone sulfonic acid or its sodium salt to hydroxyl compound used is in the range of 1:0.8 to 1:2.

29. A process according to claim 6, wherein the molar ratio of diazonaphthoquinone sulfonic acid or its sodium salt to hydroxyl compound used is in the range of 1:0.8 to 1:2.

* * * * *